United States Patent
Halverson et al.

(10) Patent No.: US 6,696,286 B1
(45) Date of Patent: Feb. 24, 2004

(54) METHOD AND DEVICES FOR DETECTING AND ENUMERATING MICROORGANISMS

(75) Inventors: Kurt J. Halverson, Lake Elmo, MN (US); Ai-Ping Wei, Woodbury, MN (US); Jean Qiu, Woodbury, MN (US); Clyde D. Calhoun, Stillwater, MN (US); James G. Berg, Lino Lakes, MN (US); James G. Bentsen, North St. Paul, MN (US); Raymond P. Johnston, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/495,092

(22) Filed: Feb. 1, 2000

Related U.S. Application Data

(60) Division of application No. 08/905,481, filed on Aug. 1, 1997, now abandoned, which is a continuation-in-part of application No. 08/838,552, filed on Apr. 9, 1997, now abandoned.

(51) Int. Cl.[7] ................................................. C12M 1/34
(52) U.S. Cl. ................................. 435/287.9; 435/287.8
(58) Field of Search ......................... 422/55, 56; 435/4, 435/6, 287.1, 287.7, 287.8, 187.9, 30, 31

(56) References Cited

U.S. PATENT DOCUMENTS

| | | | |
|---|---|---|---|
| 3,010,880 A | 11/1961 | Littman et al. | 195/103.5 |
| 3,929,583 A | 12/1975 | Sharpe et al. | 195/127 |
| 4,018,652 A | 4/1977 | Lanham et al. | 195/103.5 |
| 4,264,560 A | 4/1981 | Natelson | 422/58 |
| 4,682,891 A | 7/1987 | de Macario et al. | 356/244 |
| 4,777,021 A | 10/1988 | Wertz et al. | 422/101 |
| 4,803,154 A | 2/1989 | Uo et al. | 435/7 |
| 4,806,316 A | 2/1989 | Johnson et al. | 422/100 |
| 4,906,439 A | 3/1990 | Grenner | 422/56 |
| 5,219,462 A | 6/1993 | Bruxvoort et al. | 51/293 |
| 5,229,163 A | 7/1993 | Fox | 427/2 |
| 5,236,827 A | 8/1993 | Sussman et al. | 435/34 |
| 5,338,666 A | 8/1994 | Monthony | 435/34 |
| 5,457,030 A | 10/1995 | Badal et al. | 435/34 |
| 5,498,525 A | 3/1996 | Rees et al. | 435/29 |
| 5,503,803 A | 4/1996 | Brown | 422/102 |
| 5,700,655 A | 12/1997 | Croteau et al. | 435/30 |
| 5,707,799 A | 1/1998 | Hansmann et al. | 435/6 |
| 5,716,825 A * | 2/1998 | Hancock et al. | 435/286.5 |

FOREIGN PATENT DOCUMENTS

| | | |
|---|---|---|
| DE | 32 26 407 C2 | 5/1985 |
| DE | 36 31 066 A1 | 4/1988 |
| DE | 37 32 142 A1 | 4/1989 |
| DE | 42 18 917 A1 | 12/1993 |

(List continued on next page.)

OTHER PUBLICATIONS

Product Brochure: SimPlate™ Total Count Plate from Idexx Laboratories, Inc., undated.

*Primary Examiner*—David A. Redding
(74) *Attorney, Agent, or Firm*—Nancy M. Lambert

(57) ABSTRACT

A method for detecting a microorganism in a test sample is described. The method involves distributing microvolumes of a sample to a plurality of microcompartments of a culture device, incubating for a time sufficient to permit at least one cell division cycle of the microorganism, then detecting the presence or absence of the microorganism in the microcompartments. Also disclosed are devices for carrying out these methods.

8 Claims, 4 Drawing Sheets

FOREIGN PATENT DOCUMENTS

| | | |
|---|---|---|
| EP | 0 321 736 B1 | 6/1989 |
| EP | 0 459 093 A2 | 12/1991 |
| EP | 0 496 200 A2 | 7/1992 |
| EP | 0 656 420 A1 | 6/1995 |
| EP | 0 751 393 A2 | 1/1997 |
| EP | 0 795 600 A1 | 9/1997 |
| EP | 0 834 729 A2 | 4/1998 |
| JP | 63096558 | 4/1988 |
| JP | 04265860 | 9/1992 |
| WO | WO 92/12257 | 7/1992 |
| WO | WO 93/11727 | 6/1993 |
| WO | WO 93/19199 | 9/1993 |
| WO | WO 94/11489 | 5/1994 |
| WO | WO 95/23026 | 8/1995 |
| WO | WO 96/14432 | 5/1996 |
| WO | WO 96/15435 | 5/1996 |
| WO | WO 96/40980 | 12/1996 |
| WO | WO 97/05274 | 2/1997 |
| WO | WO 97/08291 | 3/1997 |
| WO | WO 97/12242 | 4/1997 |
| WO | WO 97/13839 | 4/1997 |
| WO | WO 97/18455 | 5/1997 |
| WO | WO 97/37036 | 10/1997 |
| WO | WO 97/49987 | 12/1997 |
| WO | WO 98/31466 | 7/1998 |

* cited by examiner

METHOD AND DEVICES FOR DETECTING AND ENUMERATING MICROORGANISMS

This is a divisional of application Ser. No. 08/905.481 filed Aug. 1, 1997 now abandoned, which is a CIP of application Ser. No. 08/838,552, filed on Apr. 9, 1997, now abandoned.

FIELD

This invention relates to methods and devices that use microvolume compartments to effect rapid and accurate detection and enumeration of microorganisms.

BACKGROUND

The detection and enumeration of microorganisms is practiced in numerous settings, including the food-processing industry (testing for the contamination of food by microorganisms such as *E. coli* and *S. aureus*), the health care industry (testing of patient samples and other clinical samples for infection or contamination), environmental testing industry, pharmaceutical industry, and cosmetic industry.

Growth-based detection and enumeration of microorganisms is commonly practiced using either liquid nutrient media (most probable number analysis (MPN)) or semi-solid nutrient media (direct counting using, e.g., agar petri dishes). Enumeration using the liquid MPN method is typically achieved by placing serial 10-fold dilutions of a sample of interest in replicate sets of tubes containing selective media and chemical indicators. The tubes are incubated at elevated temperature (24–48 hours) followed by examination for organism growth. A statistical formula, based on the number of positive and negative tubes for each set, is used to estimate the number of organisms present in the initial sample.

This method of performing MPN analysis has several disadvantages. It is labor intensive because of the multiple diluting and pipetting steps necessary to perform the analysis. In addition, it is only practical to use replicate sets of about three to five tubes for each dilution. As a result, the 95% confidence limits for an MPN estimate for microbial concentration are extremely wide. For example, a three tube MPN estimate of 20 has 95% confidence limits ranging from 7 to 89.

In contrast to the method described above, a direct count of viable microorganisms in a sample can be achieved by spreading the sample over a defined area using nutrient media containing a gelling agent. The gelling agent (agar) prevents diffusion of the organisms during incubation (24–48 hours), producing a colony in the area where the original organism was deposited. There is, however, a limit to the number of colonies that can fit on a given area of nutrient media before fusion with neighboring colonies affects the accuracy of the count. This usually necessitates performing several dilutions for each sample. In addition, the classes of chemical indicator molecules that can be used for identifying individual types of microorganisms present within a mixed population are limited to those that produce a product that is insoluble in the gelled media.

In addition to these disadvantages, both the currently used MPN analysis and gel-based systems require a relatively long incubation time before a positive result can be detected.

SUMMARY

The method of the present invention solves the problems associated with currently used systems. In general, this invention provides a method to effect rapid and accurate detection and enumeration of microorganisms based on the surprising result that the use of microvolumes substantially increases the speed of detection. As used herein, the term "microorganism" includes all microscopic living organisms and cells, including without limitation bacteria, mycoplasmas, rickettsias, spirochetes, yeasts, molds, protozoans, as well as microscopic forms of eukaryotic cells, for example single cells (cultured or derived directly from a tissue or organ) or small clumps of cells. Microorganisms are detected and/or enumerated not only when whole cells are detected directly, but also when such cells are detected indirectly, such as through detection or quantitation of cell fragments, cell-derived biological molecules, or cell by-products.

In one aspect, the invention features a method for detecting a microorganism in a liquid test sample. The method involves the steps of:

distributing microvolumes of the sample to a plurality of microcompartments of a culture device; incubating the culture device for a time sufficient to permit at least one cell division cycle of the microorganism; and detecting the presence or absence of the microorganism in the microcompartments.

As used herein, the term microvolume refers to a volume of between about 0.01 and about 25 microliters, and the term "microcompartment" refers to a compartment having a capacity, or volume, to hold a microvolume of liquid test sample.

In preferred embodiments, the method further includes the step of quantitating the microorganisms in the liquid test sample. The quantitation may include the steps of determining MPN in the sample, or it may involve enumerating the microorganisms in each microcompartment of the culture device.

In other embodiments, the microcompartments may contain a coating of nutrient medium, and the nutrient medium may further include at least one indicator substance. Alternatively, the liquid test sample may include at least one indicator substance. In either case, the indicator substance may be any indicator substance capable of providing a detectable signal in the liquid test sample. Such indicators include, but are not limited to, chromogenic indicators, fluorescent indicators, luminescent indicators, and electrochemical indicators. For purposes of this application, the term "electrochemical" means a chemical indicator that changes the resistance or conductance of the sample upon reaction with a microorganism.

In another aspect, the invention features a method for detecting a microorganism in a liquid test sample. This method involves the steps of:

distributing aliquots of the sample to a plurality of microcompartments of a culture device, wherein the culture device contains a plurality of sets of microcompartments, each set having microcompartments of uniform size and the sets varying in microcompartment size; incubating the culture device for a time sufficient to permit at least one cell division cycle of the microorganism; and detecting the presence or absence of the microorganism in the microcompartments.

In preferred embodiments, the microcompartments of these methods are of uniform size and each microcompartment has a volume of about 0.01 to about 25 microliters. More preferably, each microcompartment has a volume of about 0.1 to about 10 microliters, and even more preferably, of about 1 to about 2 microliters.

The culture device preferably contains 1 to about 100,000 microcompartments, more preferably about 100 to about 10,000 microcompartments, even more preferably about 200 to about 5,000 microcompartments, and most preferably about 400 to about 600 microcompartments.

In another aspect, the invention features an assay device. The device includes a substrate having a plurality of microcompartments therein, each microcompartment having a top and a bottom. The substrate may include a hydrophobic "land area" between the microcompartments. Preferably the microcompartments include assay reagents, for example nutrients, gelling agents or indicator substances such as chromogenic indicators, fluorescent indicators, luminescent indicators, or electrochemical indicators. To prevent formation of air bubbles when the liquid sample is loaded into the wells, some of the microcompartments may have openings at both their tops and bottoms. The bottom surface openings are occluded by a material that is permeable to air but substantially non-permeable to aqueous liquids.

In yet another aspect, the device contains microcompartments in the form of microchannels. The microchannels may be contained on a single layer or multilayer substrate, such as a film. The device may or may not have a hydrophobic land area between the microchannels. The microchannels may comprise elongate holes that are formed in the substrate. In a preferred embodiment, the microchannels are covered with a film.

The microcompartment microchannels may comprise capillary tubes. Discrete capillary tubes may be formed/bonded together to form a device. The microchannels preferably have at least one assay reagent coated thereon.

The microcompartments can be arranged in substantially parallel rows. Typically, the volumes of the microcompartments in each row are uniform. Alternatively, the microcompartments can be arranged in various groupings or patterns for easier recognition and counting of positive signals.

The volumes of the microcompartments may range from about 0.01 to about 25 microliters, more preferably from about 0.1 to about 10 microliters, and most preferably from about 1 to about 2 microliters.

As described herein, the present invention has several advantages. First, use of microvolumes in microcompartments allows for a surprisingly rapid detection of a microorganism in a liquid test sample. Second, this rapid detection allows for rapid enumeration or quantitation of microorganisms in the liquid test sample. The invention is particularly useful in MPN analysis of a liquid test sample for a particular microorganism, such as *E. coli* or *S. aureus*. The invention allows MPN analysis to be conducted conveniently in a single device, as opposed to separate tubes, and advantageously requires a substantively shorter incubation time to reach detectable microorganism growth. Third, the use of microvolumes in microcompartments allows for the separation of a liquid test sample into a relatively larger number of test volumes. In general, the use of microvolumes in microcompartments provides a far greater number of runs, or repetitions, of a test on the liquid sample. In the case of MPN analysis, use of microvolumes in microcompartments provides a greater number of data points from which the MPN can be calculated, thereby significantly narrowing the 95% confidence limits for a given MPN result. Fourth, separation of sample into a large number of test volumes allows a higher concentration of microorganisms to be enumerated, thereby reducing or eliminating sample dilutions. Fifth, this invention allows MPN analysis to be conducted in a single device having the indicators and/or nutrients directly coated thereon. Sixth, this invention permits a wide counting range when performing MPN analysis. Other advantages of the invention will be apparent from the following description and the figures.

DETAILED DESCRIPTION

Figure 1:
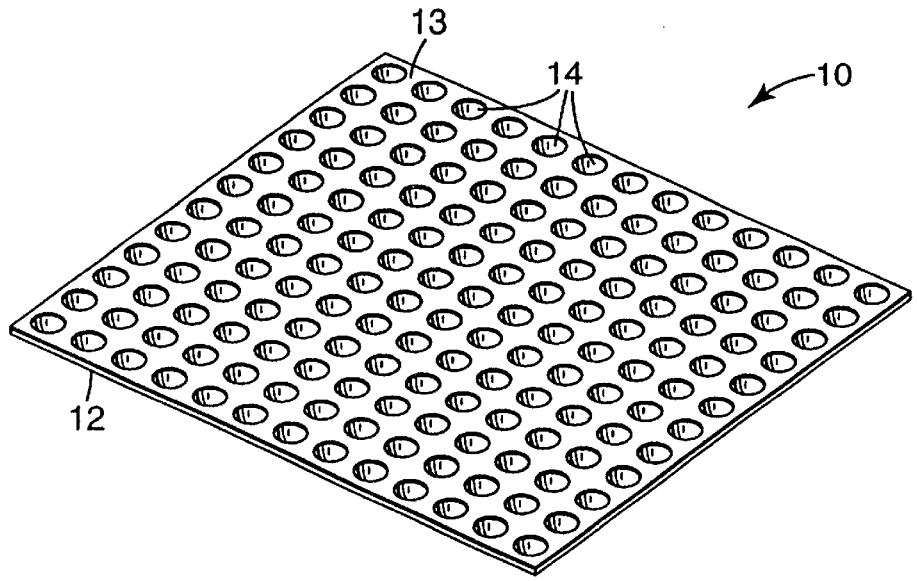
FIG. 1 is a perspective view of one embodiment of a microcompartment culture device.

This invention relates to the use of microvolume liquid sample aliquots in microcompartments in the signal-based detection of microorganisms in liquid samples.

Among the problems encountered in the art relating to the testing of liquid samples for the presence or amount of a microorganism are relatively lengthy incubation times, the need to use separate vessels for aliquots being tested, and the need for a relatively large volume of sample for testing.

The present invention provides a solution to these and other problems associated with such testing. The invention provides a method for detecting the presence, amount, or absence of a microorganism in a liquid sample by distributing microvolumes to microcompartments in a test device. A "microvolume" as that term is used herein, refers to a volume of less than about 25 microliters, and includes volumes in the sub-microliter range. The present inventors have discovered that the use of microvolumes in the detection of microorganisms in liquid samples results in remarkably shorter incubation times required to produce a detectable signal-based growth level. Because shorter incubation times are highly desirable in this field, this feature of the invention provides a distinct advantage. In addition, the use of a relatively large number of microvolume compartments significantly narrows the 95% confidence limits for the result and reduces the number of sample dilutions for concentrated samples.

In addition to the above advantages, the use of microvolumes in the testing of liquid samples may allow for the use of substantially smaller test samples. Very small volume test samples are sometimes necessary due to very small volume sample sources or desirable for purposes such as ease of handling.

The present inventors have developed a number of novel devices for microvolume-based testing of liquid samples. Non-limiting examples of these devices include a substrate, such as micro-embossed or pressed films having a plurality of microcompartments and having various surface treatments to improve performance and convenience and micro-embossed or pressed films having a plurality of open-bottomed microcompartments, wherein each well bottom opening is occluded by a material that is permeable to air but is substantially non-permeable to aqueous fluids. The open bottomed configuration may help to eliminate the potential problem of air bubbles being entrapped in the sample in the microcompartments.

When viewed in a top view, the microcompartment may have, for example, a generally circular, faceted, square, oval, or elongate appearance. It will be appreciated that the microcompartments of these devices may have many possible shapes, such as cylindrical, conical, pyramidal, hemispherical, tetrahedral, cubic, truncated shapes, and the like, with open or closed bottoms.

Another example includes a substrate, such as a plastic film containing microchannels, wherein the liquid sample may move into the microchannels by capillary action. The microchannels may be discrete capillary tubes that are formed or bonded together into a substrate. The cross section of each channel may take many shapes, including circular, triangular, square, and rectangular shapes and the like. In a preferred embodiment, the cross section of the end(s) of the microchannels is smaller than the cross section of the middle of the microchannels. In this configuration, sample is less likely to spill out during handling of the devices.

Advantageously, the above-summarized devices allow for the testing of liquid samples using microvolume aliquots in a single device, eliminating the need for separate vessels. A test sample may be distributed among hundreds or thousands of discrete microcompartments, thereby substantially increasing the number of data points in a liquid sample test.

A particularly useful application of these methods and devices is in the growth-based detection and enumeration of microorganisms in liquid test samples. Such growth-based detection and enumeration is very important in the testing of food, environmental, clinical, pharmaceutical, cosmetic, and other samples for contamination by microorganisms. The methods and devices of this invention allow for the efficient, accurate, convenient, and cost-effective testing of such samples.

A preferred use of the methods and devices of this invention is in MPN. The amount of labor is greatly reduced because no pipetting into individual tubes is necessary. Instead, the liquid sample is distributed to microcompartments by methods such as loading a single device and spreading the sample over the microcompartments. In addition, fewer sample dilutions are necessary because of the large number of microcompartments in the devices. The relatively large number of microcompartments also provides a more accurate microbial concentration estimate. This is because the correspondingly larger number of data points provides a correspondingly narrower confidence limit interval.

Accordingly, the present invention provides a method for detecting a microorganism in a liquid test sample. The method first involves distributing microvolumes of the test sample to a plurality of microcompartments of a culture device. The culture device may be any device that contains a plurality of microcompartments and that can be loaded with the liquid test sample. Non-limiting examples of such culture devices include those described herein.

The microcompartments in the culture device preferably are of uniform size and each microcompartment has the capacity to hold a volume of about 0.01 to about 25 microliters of the liquid sample. In a preferred embodiment, each microcompartment has a volume of about 0.1 to about 10 microliters. In another preferred embodiment, each microcompartment has a volume of about 1 to about 2 microliters. The culture device preferably contains about 1 to about 100,000 microcompartments, more preferably about 100 to about 10,000 microcompartments, even more preferably about 200 to about 5,000 microcompartments and most preferably about 400 to about 600 microcompartments.

The use of a device having about 400 to about 600 microcompartments is particularly useful in the context of testing a liquid sample for microorganism concentration using MPN. Certain regulatory requirements may dictate that a testing method must be able to detect one microorganism in a one to five milliliter sample. Such a sample size is standard in the food processing industry for microbiological testing. Thus, for example, a culture device having 500 microcompartments, wherein each microcompartment has a volume of about 2 microliters, would be very useful for testing a 1-ml sample. The microcompartment size of 2 microliters allows for rapid development of a detectable signal in accordance with the invention, and the use of about 400 to about 600 microcompartments provides a sufficiently large number of data points to substantially improve the confidence interval for an MPN calculation. In addition, it is feasible to perform a manual count of microcompartments testing positive for the microorganism of interest.

The liquid test sample may be any sample containing microorganisms from any source. The sample may be distributed to the plurality of microcompartments directly, or the sample may be diluted before distribution to the microcompartments. The determination as to whether sample dilution is necessary will depend on a variety of factors such as sample source and age, and such determination is a routine matter to those of skill in the art.

The liquid test sample may include selective nutrient growth media, optionally including a gelling agent, for the microorganism of interest and/or an indicator substance that produces a signal in the presence of the growing microorganism. A gelling agent is a water absorbing material that becomes a gel upon the addition of water. If a gelling agent is used, the gel preferably will encapsulate, or contain, the growing microorganism. One or both of the selective nutrient growth medium and the indicator substance may be present in the microcompartments, in amounts sufficient to achieve desired concentrations when a microvolume of the liquid test sample is distributed into the microcompartments. The coating may be achieved, for example, by placing or distributing a solution of the nutrient medium and/or indicator substance into the microcompartments and dehydrating the solution to produce a coating of the nutrient medium and/or indicator substance in the microcompartments.

A wide variety of selective growth media for a wide variety of microorganisms of interest is known, as is a wide variety of indicator substances for a wide variety of microorganisms, and any of these media or indicator substances might be suitable for use in the method of the invention. Soluble indicators can be used in the present invention, because diffusion is prevented by confinement within the microcompartments.

The method by which the liquid test sample is distributed to the plurality of microcompartments depends on the particular culture device employed in the method. If a film device containing microcompartments is used, the sample may simply be poured or pipetted over the device and the sample spread over the microcompartments with, for example, agitation, a blade, or other tool. If microchannels are used, the sample may be distributed into the microchannels via capillary action.

After the sample is distributed to the microcompartments of the culture device, the culture device is optionally covered or sealed to enclose the microcompartments and then is incubated for a time sufficient to permit at least one cell division cycle of the microorganism. In general, incubation of the culture device is conducted at about 25–45° C. preferably at about 30–37° C. In the practice of this invention, in which microcompartments are used, the incubation time will vary. For example, when detecting and enumerating most bacteria, the incubation time will typically range from about 20 minutes to about 24 hours in order to produce detectable growth as demonstrated by the indicator substance in the incubated liquid test sample. This relatively short incubation time represents a distinct advantage over detection methods currently used, which typically require incubation times of about 24 hours or more.

Following incubation of the culture device, the presence or absence of the microorganisms in the microcompartments (and thus in the liquid test sample) is detected. The mode and sensitivity of detection depends on the type of indicator substance used in the method. In some instances, the presence or absence of the microorganism may be detected visually without the aid of signal-generating indicator substance, by visualizing the turbidity or clarity of the sample in each microcompartment. Any indicator substance that provides a detectable signal in the liquid test sample may be used, including but not limited to chromogenic indicators, fluorescent indicators, luminescent indicators, electrochemical indicators, and the like. The presence or absence of a microorganism in a microcompartment may be visually detected, with the naked eye, microscopically, or with the aid of other equipment or, methods. There are numerous indicator substances and signal detection systems known in the art for detecting microorganisms, and any such substance or system may be used in accordance with the present invention.

The detection of microorganisms in the liquid sample may further involve the enumeration of a microorganism count in the liquid test sample. In a preferred embodiment, the enumeration is performed using MPN. Once the number of microcompartments containing the microorganism of interest is determined, an MPN calculation can be made using known MPN techniques. If desired, the number of microorganisms in an individual microcompartment can then be determined using known techniques, for example, signal intensity compared to a known standard, or by plating the contents of the microcompartment. Advantageously, the large number of microcompartments used in the method of the invention allows for narrower intervals for the 95% confidence limits in an MPN analysis of a liquid test sample.

Because of the large number of microcompartments in a single device that the methods and devices of the present invention provide, it is possible to use a single device in the detection and enumeration of multiple microorganisms of interest, while retaining the advantages of the invention. For example, a single liquid test sample could be tested for the presence or concentration of *E. coli* and *S. aureus*. One portion of a culture device could contain microcompartments for the detection and enumeration of one of these microorganisms by, for example, coating one set of microcompartments with selective growth medium and a first indicator substance selected to detect that microorganism. A second set of microcompartments could be coated with selective growth medium and a second indicator substance selected to detect another microorganism of interest. Alternatively, all microcompartments of a culture device could be coated with assay reagents designed for the simultaneous detection of multiple microorganisms. For example, *E. coli* could be detected with a fluorescent indicator substance while, at the same time, coliforms could be detected with a chromogenic indicator substance.

In another embodiment, the invention relates to a method for detecting a microorganism in a liquid test sample. The method is similar to the method described above, except that the distribution step involves distributing microvolumes of the liquid test sample to a plurality of microcompartments of the culture device, wherein the culture device includes a plurality of sets of microcompartments. Each set of microcompartments has compartments of uniform size, and the device has at least two sets of microcompartments. For example, the culture device could include a plurality of lanes or other groupings, each containing microcompartments of a particular volume. This feature allows for the distribution of the liquid test sample into different test volume sizes, including volume sizes greater than microvolume size, within a single device. In MPN, this feature provides a significant advantage in that, for a highly concentrated sample, an appropriate volume size may be selected and MPN analysis performed using a single distribution step in a single device without the need for serial dilutions.

As stated above, the methods of this invention may be practiced using any culture or test device containing microcompartments, depending on the particular embodiment being practiced. The present inventors have developed several novel devices suitable for use in the methods of this invention. The following are non-limiting examples of such devices.

Referring to FIG. 1, a device 10 may comprise a substrate 12 having a plurality of compartments in the form of microcompartments 14. The substrate 12 can be fabricated from any material in which microcompartments can be fashioned. Substrate 12 can be fabricated, for example, from polymeric films or other appropriate materials. Appropriate polymers include without limitation polyethylene, polypropylene, polyamides, fluoropolymers, polycarbonates, polyesters, polyurethanes, and polystyrenes. Microcompartments 14 can be formed by any process appropriate to the substrate 12 material. Such processes include without limitation thermal embossing, cast embossing, laser drilling, and etching with reactive materials. Alternatively, a device may be prepared by laminating a sheet of patterned material containing a plurality of small openings onto a support film, wherein a microcompartment is formed by the combination of the opening and the support film. Polyethylene or polypropylene films can be, for example, pressed embossed or extrusion embossed, and can include various pigments and surfactants.

Figure 2:
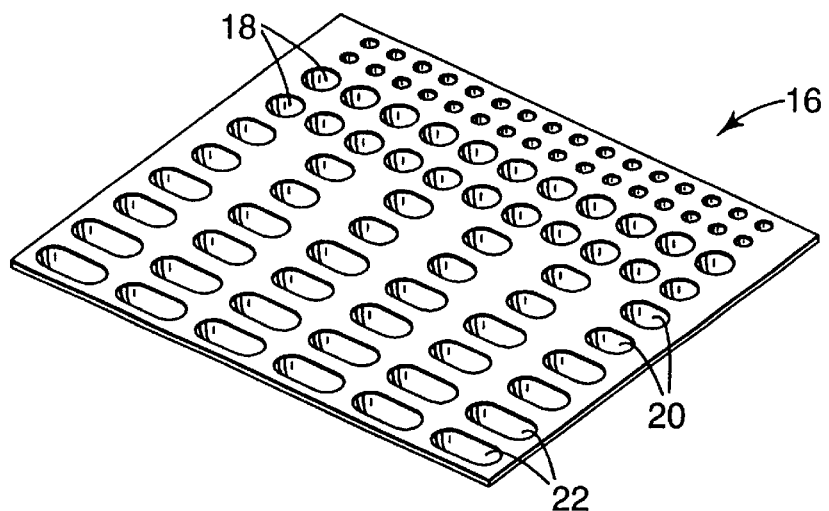
FIG. 2 depicts a top view of a microcompartment culture device having sets of microcompartments varying in microcompartment volume.

The device 10 may include any desired number of microcompartments. Additionally, the device 10 may include relatively large reservoirs or other compartments adapted to hold larger volumes of liquid for maintenance of an appropriate humidity level within the device. Although the number of microcompartments can be relatively small (e.g., 2–50), the small sizes of the microcompartments allow relatively large numbers of microcompartments to be fabricated on a single device 10. Preferably, the device has about 1 to 100,000 microcompartments, more preferably about 100 to about 10,000 microcompartments, even more preferably between about 200 to about 5,000 microcompartments, and most preferably about 400 to about 600 microcompartments. The device 10 can have a population of uniformly sized microcompartments 14, although the microcompartments need not be of uniform size. For example, a device 16 as depicted in FIG. 2 can have sets (e.g., rows) of microcompartments in which volumes are constant within a set, but vary between sets. As depicted in FIG. 2, the volumes can vary incrementally over an array of sets of microcompartments, with the smaller microcompartments 18 holding sub-microliter volumes and the larger microcompartments 20 holding multiple-microliter volumes. It is even possible for the largest microcompartments in a device such as depicted in FIG. 2 to include microcompartments 22 that would not be classified as "microcompartments." Such microcompartments might hold, for example substantially more than 25 microliters up to milliliter volumes.

Assay reagents can be coated within the microcompartments of the device. Such assay reagents can include without limitation nutrients for growth of microorganisms, gelling agents, indicator substances such as chromogenic indicators, fluorescent indicators, luminescent indicators, and electrochemical indicators. The assay reagents can be immobilized in the microcompartments by any of numerous methods for immobilizing assay reagents on solid substrates known to those of skill in the art. Such methods include for example drying down assay reagent-containing liquids in the microcompartments, as well as other methods for noncovalently attaching biomolecules and other assay reagents to a solid substrate.

Figure 3:
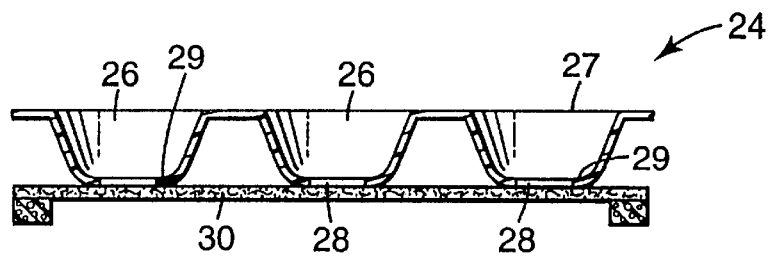
FIG. 3 is a side view of a microcompartment device having open microcompartment bottoms occluded by nonwoven web material.

In a preferred embodiment, the microcompartments are fabricated to prevent entrapment of air bubbles when the microcompartments are loaded with aqueous sample liquids. This can be accomplished, for example, by fabricating the well bottom openings to be permeable to air while at the same time being substantially impermeable to aqueous liquids. One such embodiment is depicted in FIG. 3. In this embodiment, an assay device 24 contains microcompartments 26 having tops 27 and bottoms 29 which are prepared with holes 28 through the bottoms. These holes are occluded (plugged or covered) with material 30 that is permeable to air but substantially impermeable to aqueous sample liquids. The occluding material can be any composition having the desired permeability characteristics. In the preferred embodiment depicted in FIG. 3, the occluding material is a non-woven web 30 bonded to the bottom 29 of the microcompartment 26. Preferably the non-woven web 30 is a blown-fiber pressure-sensitive adhesive material that is easily bonded to bottom 29 by means of pressure. During loading of sample into the microcompartments 26, bubbles either do not form or rapidly dissipate after formation, leaving each well with about the same volume of liquid sample as depicted in FIG. 3.

As discussed above, the presence of microcompartments in an assay device allows for separation of a liquid test sample into a relatively large number of test microvolumes. The ability to separate a liquid sample into microcompartments and to perform MPN or other assays without cross-contamination between compartments is a major advantage of the present devices. Various additional fabrication methods, however, can be used to further enhance the separation function of the microcompartments, as described below.

Referring again to FIG. 1, the area 13 between microcompartments 14 ("land area") may be fabricated to be hydrophobic. This serves to prevent aqueous fluid from bridging between the microcompartments 14, thereby preventing cross-contamination. The land area 13 can be rendered hydrophobic in various ways. For example, the land area on an extrusion embossed polyethylene film, that had been rendered hydrophilic by incorporation of a surfactant, can be rendered hydrophobic by transferring a thin layer of acrylated silicone or other hydrophobic material to the land area.

Figure 6:
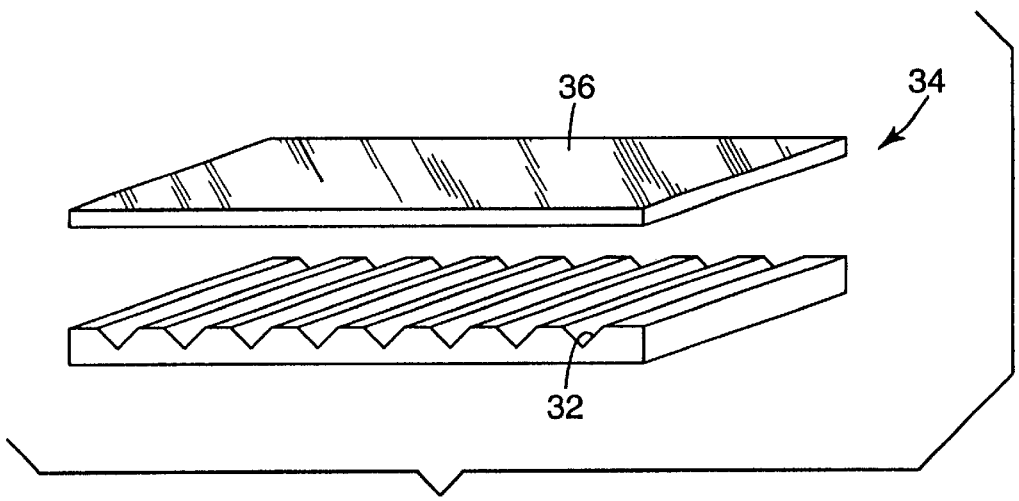
FIG. 6 is an exploded perspective view of a single layer microcompartment device having microchannels.

Referring to FIG. 6, the microcompartments may be fashioned as microchannels 32 in a substrate 34. The shape of the microchannel 32 may vary. The microchannel may be square bottomed, U- and V-shaped or comprise elongate holes.

Preferably, microchannel 32 is covered to prevent evaporation from the channel and contamination of the channel. The cover 36 may be prepared from any suitable material that is at least partially impermeable to water vapor. For example, the cover may comprise a silicone pressure-sensitive adhesive film or a heat sealable film.

Assay reagents may be coated into the microchannel. Preferably, at least one such reagent is coated into each microchannel.

Figure 7:
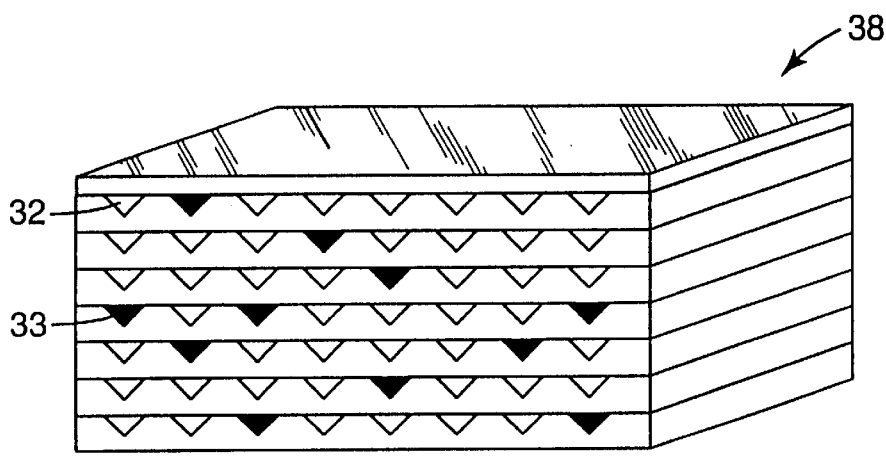
FIG. 7 is a perspective view of a multi-layered microcompartment device having microchannels.

In an alternative preferred embodiment as depicted in FIG. 7, individual layers of film with microchannels 32 therein can be laminated together to form a multi-layered structure 38. This structure has many advantages, including having a large number of microcompartments in a small area and ease of innoculation of a large number of microcompartments. As depicted, the shaded channels 33 represent channels having a positive indication for the target microorganism.

Figure 8:
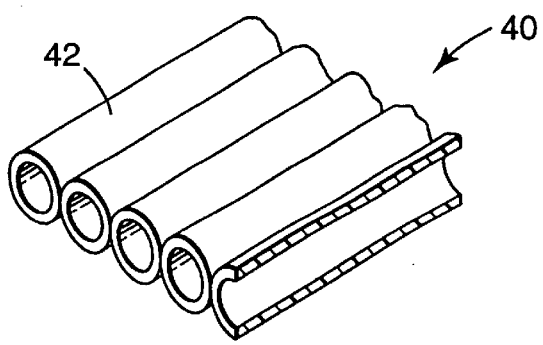
FIG. 8 is a cross-sectional view of a single layer micrcompartment device having microchannels.

Alternatively, as depicted in FIG. 8, the device 40 may comprise a plurality to of capillary tubes 42 that are bonded or formed together into a substrate, as depicted in FIG. 7. The capillary tubes may be open-ended or may be partially closed at one end.

All references and publications cited herein are expressly incorporated herein by reference into this disclosure. Particular embodiments of this invention will be discussed in detail and reference has been made to possible variations within the scope of this invention. There are a variety of alternative techniques and procedures available to those of skill in the art which would similarly permit one to successfully practice the intended invention.

EXAMPLES

The following examples are offered to aid in understanding of the present invention and are not to be construed as limiting the scope thereof. Unless otherwise indicated, all parts and percentages are by weight.

Example 1

Embossed Film Culture Devices

Embossed film culture devices containing a plurality of microcompartments and capable of being used for the detection of microorganisms in a liquid test sample were constructed as described in this example.

The microcompartments can be formed in a substrate by a number of processes, examples of which are thermal embossing, cast embossing, laser drilling, and by etching the surface with a reactive material. Detailed descriptions of how to make recesses (i.e., "microcompartments") in polymeric films are provided in U.S. Pat. Nos. 5,192,548; 5,219,462; 5,344,681; and 5,437,754. The following descriptions are representative of specific embossed film culture devices used in the subsequent examples.

A. Pressed Embossed Films Containing a Plurality of Microcompartments

Polyethylene (Eastman Chemical Company Resin #18BOA) containing 10% by weight $TiO_2$ (50% $TiO_2$/50% Polyethylene Pigment Concentrate) and 0.5% by weight Triton X-35 Surfactant (Sigma Chemical Company) was extrusion cast into a film (4-mil thickness). The film was cut into sheets and stacked (~20 sheets) onto photolithographically etched magnesium alloy tooling prepared as described in U.S. Pat. No. 5,192,548, designed to form a plurality of microcompartments. The etched magnesium tooling contained protuberances arranged in the patterns described in subsequent examples. The stacked polyethylene sheets were embossed on a heated hydraulic press (132° C., 120 second dwell) as described in U.S. Pat. No. 5,219,462. The samples were allowed to cool, at which time the tooling was removed to provide a single layer film containing the "negative" image of the tooling.

B. Extrusion Embossed Films Containing a Plurality of Microcompartments

A sheet of photolithographically etched magnesium master tooling was attached to a steel roll using pressure-sensitive transfer adhesive. The polyethylene, pigment, and surfactant composition described in example 1A was blended together and extrusion cast onto the roll as described in U.S. Pat. No. 5,192,548, which is incorporated herein by reference. Samples lacking the Triton X-35 were also prepared in this manner.

C. Extrusion Embossed Films With Hydrophobic "Land" Area

Extrusion embossed polyethylene films containing Triton X-35 Surfactant were prepared according to Example 1B. The area between microcompartments ("land" area) was rendered hydrophobic by transferring a thin layer of acrylated silicone (Goldschmidt FC 711) containing 4.8% of a cross linking agent (Darocur 1173) using a roll-to-roll coating apparatus (Straub Design Co.). The hydrophobic coating was cured by exposing the film to ultraviolet radiation under nitrogen atmosphere using a Fusion Systems UV lamp with an H bulb providing a dosage of 85 millijoules /$cm^2$. An aqueous solution containing phenol red indicator (to provide contrast) was spread over treated and untreated samples. The samples treated with the hydrophobic coating were shown to partition liquid into individual microcompartments without fluid bridging between the microcompartments.

D. Pressed Embossed Films Containing a Plurality of Microchannels

Polyethylene film (Example 1A) was cut into sheets and stacked (~10 four-mil sheets) onto magnesium tooling designed to form a plurality of parallel microchannels, followed by embossing on a heated hydraulic press according to the following protocol: heated to 143° C., held at 0.7 N/$m^2$ for 1 minute, pressure increased to 2.8 N/$m^2$ and held for 1 minute, pressure decreased to 2.1 N/$m^2$ and held for 15 seconds, cooled to 29° C., and released. The tooling was removed to provide a single layer film containing the "negative" image of the tooling. After embossing, a polyester (PE) backing material containing a silicone pressure sensitive adhesive (PSA) (CW14HT, Specialty Tapes, Racine, WI) was laminated to the top of the embossed film, thereby creating a series of parallel, covered microchannels.

Example 2

Embossed Film Culture Devices With Bottom-Perforated Microcompartments

Embossed film culture devices containing a plurality of bottom-perforated microcompartments, and having the openings in the bottom covered with a non-woven web backing, were constructed as described in this example. Test sample filling efficiencies and leaking of these culture devices were evaluated as also described in this example.

A. Preparation of Bottom-Perforated Embossed Film Culture Devices

Polypropylene (18-mil thick, Conplex Co) was embossed as described in Example 1A, but with an embossing tool designed to produce microcompartments having very thin (<1-mil thick) bottom layers. Heat from a propane torch was then applied to the bottom surface of the microcompartments to generate a hole (perforation). The diameter of the hole formed in this manner is smaller than the diameter of the bottom of the original microcompartment.

Fill and Leak Testing of Bottom-Perforated Embossed Film Culture Devices

To test for filling efficiency and leaking, a test sample (1.5–3.0 ml) of Butterfield diluent (Weber Scientific, Hamilton, N.J.) containing phenol red to aid in visual inspection was applied by pipette onto a polypropylene embossed film having a plurality of microcompartments, some of which were perforated as described above. Each microcompartment was in the shape of an inverted truncated hexagonal cone, having a diameter of approximately 1.9 mm at the surface and 1.0 mm at its depth, which was about 1.1 mm. The solution was distributed over the microcompartments by swirling the embossed film by hand. It was observed that nearly all of the microcompartments with perforated bottoms were filled with the test solution and had no apparent air bubbles. In comparison, occasionally the microcompartments without perforated bottoms were observed to contain entrapped air bubbles. However, when the bottom surface of the embossed film was placed in contact with a second surface, test solution was wicked out of the microcompartments containing open bottoms. Also, during the inoculation process, it was observed that the test solution applied from a pipette at high speed sometimes leaked through the few microcompartments located directly under the tip of the pipette.

Preparation-of Embossed Films With Bottom-Perforated Microcompartments Covered With Non-Woven Webs A pressure sensitive adhesive (PSA) non-woven web material was applied to the underneath surface of the embossed polypropylene film culture devices having a plurality of bottom-perforated microcompartments in order to eliminate leaking of the test sample solution. The non-woven web was constructed of Kraton 1112 (web weight=50 g/$m^2$) and contained a blown-fiber PSA as described in European Patent Application No. 94119851.7. The PSA non-woven web was easily bonded to the film by pressure and, thereby, formed a covered, but air-porous, bottom on each of the microcompartments.

Fill and Leak Testing of Films With Bottom-Perforated Microcompartments Covered With Non-Woven Webs Butterfield diluent containing phenol red, as described above, was inoculated onto a polypropylene embossed film having a plurality of microcompartments, some of which were perforated and covered on the bottom with a non-woven web. All perforated microcompartments were filled by a simple hand-swirling of the film, and only non-perforated microcompartments entrapped air. Different amounts of test solution (1–3 ml) were applied by pipette with no leaking observed during the inoculation process. No flow of test solution through the porous, covered bottom of the microcompartments was observed under an optical microscope, and when the film was placed in contact with a second surface, no wicking of the test solution was apparent.

B. Laminated Sheets With Open-Bottom Microcompartments Covered With Non-Woven Webs Laminated sheets containing a plurality of open-bottom microcompartments, and having the well bottom openings covered with a non-woven web backing, were constructed as described in this example. These laminated sheets can be cut to size and utilized in culture devices for the detection and enumeration of microorganisms.

Polyethylene film containing a plurality of small, uniformly spaced openings (Vispore 6607 and Vispore 6582, Tregedar Film Products, Richmond, Va.) was laminated onto a non-woven PSA web to provide laminated sheets containing a plurality of microcompartments with open bottoms covered with a non-woven web. Physical characteristics of the starting film materials are summarized in Table 2B.

TABLE 2B

| Film Materials | | |
|---|---|---|
| | Vispore 6607 | Vispore 6582 |
| Number of Openings per cm$^2$ | 14 | 285 |
| Diameter of Openings (mils) | 59 | 13 |
| Film Thickness (mils) | 35 | 13 |
| Calculated Volume of Opening ($\mu$l) | 1.4 | 0.03 |

The laminated sheets were easily inoculated by adding a small volume of nutrient solution containing phenol red to enhance visualization of the filled microcompartments. Magnified optical images of the laminated sheets after inoculation showed uniform filling of the microcompartments. No air bubbles or leaking were observed in the filled microcompartments, thereby suggesting that air, but not liquid, could flow readily through the non-woven web-covered bottom openings of the microcompartments.

Example 3

Detection and Enumeration of Microorganisms
(Method Utilizing Plurality of Microcompartments)

The feasibility of utilizing embossed film culture devices containing a plurality of microcompartments to detect and enumerate *E. coli* was demonstrated in this example.

An overnight broth culture of *E coli* ATCC 51813 (~10$^9$ CFU/ml in Tryptic Soy Broth (TSB) media) was serially diluted into Violet Red Bile (VRB) media (7.0 g/l Bacto peptone, 3.0 g/l yeast extract, and 1.5 g/l bile salts) containing 4-methylumbelliferyl-β-D-glucuronide (0.5 mg/ml) (MUG, Biosynth International, Naperville, Ill. ). The dilutions were prepared to the approximate bacterial concentrations shown in Table 3a. A diluted sample (1 ml) was applied by pipette onto a polyethylene embossed film culture device (Example 1B, lacking the Triton X-35) containing 525 microcompartments (about 1.9 $\mu$l/microcompartment). The microcompartments were arranged in a hexagonal array (about 19 microcompartments /cm$^2$) and each microcompartment was in the shape of an inverted truncated hexagonal cone, having a diameter of approximately 1.9 mm at the surface and 1.0 mm at its depth, which was about 1.1 mm. The microcompartments were filled as described in U.S. Pat. No. 5,219,462 by guiding the diluted sample solution down the film with the edge of a razor blade. A diluted sample (1 ml) also was placed on a PETRIFILM™ Series 2000 Rapid Coliform Test Plate (3M Company, St. Paul, Minn.), incubated, and read according to manufacturer's directions. The inoculated embossed film culture devices were placed inside petri dishes, and incubated for 12 hours at 37° C. The number of microcompartments exhibiting fluorescence were counted for each sample. The most probable number was calculated using the formula MPN=N ln (N/N−X) where N is the total number of filled microcompartments and X is the total number of microcompartments showing a positive reaction. The results are compared with counts from the PETRIFILM™ Series 2000 Plates in Table 3a.

TABLE 3a

| Enumeration of Microorganisms (*E. coli*) | | | |
|---|---|---|---|
| Final Dilution | Positive Micro- compartments | MPN/ml | PETRIFILM ™ Series Count 2000 Plates |
| 1 × 10$^{-4}$ | 525 | >3,300 | TNTC* |
| 1 × 10$^{-5}$ | 525 | >3,300 | TNTC |
| 5 × 10$^{-4}$ | 525 | >3,300 | TNTC |
| 1 × 10$^{-4}$ | 465 | 1,138 | TNTC |
| 5 × 10$^{-7}$ | 348 | 571 | 350 (estimate) |
| 5 × 10$^{-8}$ | 36 | 37 | 37 |
| 5 × 10$^{-9}$ | 6 | 6 | 3 |

*TNTC = Too Numerous To Count

The results of this example show that microorganisms can be readily detected and enumerated using an embossed film culture device having a plurality of microcompartments and that values obtained are comparable with those obtained from commercial PETRIFILM™ Series 2000 Count Plates. In addition, this method provides a broader counting range per sample than currently available methods.

Example 4

Detection and Enumeration of Microorganisms
(Method Utilizing Bottom-Perforated Microcompartments)

The feasibility of utilizing embossed film culture devices containing a plurality of microcompartments, which were perforated and covered on the bottom with a non-woven web, for the detection and enumeration of *Serratia marcescans* was demonstrated in this example.

An overnight broth culture of *Serratia marcescans* grown at 35° C. in TSB was serially diluted by 10-fold increments in Butterfield's diluent. The 10$^{-4}$, 10$^{-5}$ and 10$^{-6}$ dilutions were used to inoculate polypropylene embossed film culture devices having bottom-perforated microcompartments covered with a nonwoven web (Example 2). Each film was cut into 5.1-cm diameter circles and placed in polystyrene petri dishes (5.1-cm diameter×1.9-cm height) for inoculation, growth and detection of bacteria. The film disc was elevated from the bottom of the petri dish by a foam spacer ring. Curable silicone was applied along the edge of the film disc edge to provide a seal between the film disc and the dish. The seal prevented test sample solutions from leaking through the edge of the film disc during inoculation. Each of the resulting culture device plates contained about 300 microcompartments (about 2.0 $\mu$l/well) and was treated by soaking in isopropanol for 2 to 3 minutes and dried overnight at ambient conditions and in an oven at 60° C. for 5 minutes prior to use.

A sample (0.1 ml) from the individual dilutions was mixed with balanced aerobic count nutrient medium (0.9 ml) having the composition shown in Table 4a and containing 4-methylumbelliferylphosphate (0.1 mg/ml). The resulting test sample (~1 ml) was applied by pipette onto a culture device plate and the plate was gently agitated to deposit a portion of the sample into each of the microcompartments. The plate was then tilted to pour out the excess sample volume into an absorbent pad that was attached to the rim of the polystyrene dish. Additional distilled water (about 0.3 ml) was added to the absorbent pad to moisten it completely to provide a humidity reservoir. The inoculated plates were inverted, incubated for 24 hours at 35° C., and the number of fluorescent (positive) microcompartments counted under UV light (360 nm) excitation. Most Probable Number (MPN) was calculated according to Example 3. The MPN/ml was calculated by multiplying the MPN by 1.66 based on a sampled volume of 600 microliters contained within the 300 microcompartments of the device. Results are provided in Table 4b.

TABLE 4a

Balanced Aerobic Count Nutrient Medium

| Ingredient | Concentration (g/l) |
|---|---|
| Sodium Pyruvate (Sigma Chem Co., St. Louis, MO) | 4.4 |
| Tryptone (Difco Labs, Detroit, MI) | 7.5 |
| Yeast Extract (Difco Labs) | 2.5 |
| Glucose, Anhydride (Sigma Chem Co.) | 3.6 |
| Beef Extract (Difco Labs) | 1.0 |
| $KH_2PO_4$ (Sigma Chem Co.) | 1.1 |
| $Na_2HPO_4$ Anhydride (Sigma Chem Co.) | 6.0 |
| $MgSO_4.7H_2O$ (Matheson, Coleman & Bell, Norwood, OH) | 1.0 |

TABLE 4b

Enumeration of Microorganisms (*Serratia marcescans*)

| Final Dilution | Number of Positive Microcompartments | MPN/ml |
|---|---|---|
| $1 \times 10^{-5}$ | 298 | 2504 |
| $1 \times 10^{-6}$ | 151 | 348 |
| $1 \times 10^{-7}$ | 26 | 43 |

The results of this example show that microorganisms can be readily detected and enumerated using an embossed film culture device having a plurality of microcompartments, which were perforated and covered on the bottom with a non-woven web. The web-covered openings in the bottom of the microcompartments allowed air, but not liquid, to escape when the liquid sample was applied. The number of bacteria detected (positive microcompartments or MPN) correspondingly decreased for each serial dilution.

Example 5

Detection and Enumeration of Microorganisms (Method Utilizing Sets of Microcompartments)

The feasibility of utilizing embossed film culture devices containing a plurality of microcompartments of different sizes ("sets") to detect and enumerate *E. coli* was demonstrated in this example.

Diluted samples of *E. coli* ATCC 51813 were prepared according to Example 3. Two embossed film culture devices were prepared according to Example 1B. The first contained a square array of 0.8-$\mu$l microcompartments (~16 microcompartments/cm$^2$), each microcompartment in the shape of an inverted truncated cone, having a diameter of approximately 1.2 mm at the surface and 0.7 mm at its depth, which was about 1.0 mm. The second film contained a square array of larger 5-$\mu$l microcompartments (~4 microcompartments/cm$^2$), each microcompartment in the shape of a truncated square pyramid, having an opening of 3.7×3.7 mm at the surface and 2.0×2.0 mm at its depth, which was about 1.0 mm. A 250-$\mu$l sample of each dilution was partitioned into the microcompartments by using the procedure described in Example 3. The devices were incubated overnight at 37° C. and the number of microcompartments exhibiting fluorescence was counted for each set of films. MPN values were calculated as described in Example 3. The MPN per milliliter was calculated by multiplying the value obtained for the 250-$\mu$l inoculum by 4. Results are provided in Table 5a and are compared with counts obtained from standard testing with PETRIFILM™ Series 2000 Count Plates.

TABLE 5a

Enumeration of Microorganisms (*E. coli*)

| Final Dilution | Positive 0.8-$\mu$l Microcompartments | MPN/ml (0.8 $\mu$l) | Positive 5-$\mu$l Microcompartments | MPN/ml (5 $\mu$l) | PETRIFILM™ Series 2000 Plates |
|---|---|---|---|---|---|
| $1 \times 10^{-5}$ | 300 | >6844 | 50 | >782 | TNTC |
| $5 \times 10^{-6}$ | 300 | >6844 | 50 | >782 | TNTC |
| $1 \times 10^{-6}$ | 300 | >6844 | 50 | >782 | TNTC |
| $1 \times 10^{-7}$ | 292 | 4,349 | 50 | >782 | TNTC |
| $5 \times 10^{-8}$ | 64 | 286 | 41 | 342 | 213 |
| $2.5 \times 10^{-8}$ | 36 | 155 | 31 | 193 | 136 |

The results of this example show that microorganisms can be readily detected and enumerated using an embossed film culture device having a plurality of microcompartments of different sets and that values obtained are comparable with those obtained from commercial PETRIFILM™ Series 2000 Count Plates. This example further demonstrates that a wider counting range can be obtained using a set of "small" microcompartments coupled with a set of "large" microcompartments.

Example 6

Detection and Enumeration of Microorganisms (High Counting Range)

This example demonstrates a detection and enumeration method for a highly concentrated sample (>200,000 CFU/ml).

VRB nutrient media containing 1 mg/ml 5-bromo-4-chloro-3-indoxyl-$\beta$-D-glucuronic acid (BCIG, Biosynth International, Naperville, Ill.) and glucose (1 g/l) was prepared according to Example 3. An overnight culture of *E. coli* ATCC 51813 was diluted into this media formulation to an approximate concentration of 1,000 CFU/ml.

A film containing approximately 2,330 microcompartments per square inch (0.03 microliters per microcompartment) was prepared according to Example 1A. Each microcompartment was in the shape of an inverted truncated hexagonal cone, having a side-to-side diameter of approximately 0.3 mm at the surface and 0.15 mm at its depth, which was 0.7 mm. The microcompartments were filled as described in Example 3 by guiding the inoculum over the microcompartments with the edge of a razor blade. For this example, a silicone pressure-sensitive adhesive tape (Product #CW-14HT, Specialty Tapes, Racine, Wis.) was used to seal the tops of the microcompartments. This method provided a means to prevent evaporation of the small volumes of sample in the microcompartments during overnight incubation. The sealed film was incubated at 37° overnight (18 hours) then subsequently removed from the incubator and observed under a microscope. The number of positive microcompartments (blue color) was counted in a representative microscope field containing 520 microcompartments, corresponding to a sampled volume of 15.6 microliters. Nineteen positive microcompartments were observed in the field, corresponding to a calculated MPN value of 1,290 per ml. The maximum counting range for this example (519 positives for a sampled volume of 15.6 microliters) was 208,000 CFU/ml.

Example 7

Detection and Enumeration of Microorganisms (Method Utilizing a Plurality of Coated Microcompartments)

This example demonstrates the method wherein nutrient and indicator are incorporated into the microcompartments of the film prior to inoculation with test sample.

VRB media containing MUG fluorescent indicator was prepared as described in Example 3. An excess of this solution was applied to the surface of a film with the microcompartment pattern and geometry described in Example 3. The solution was distributed into the microcompartments by knife coating the solution over the surface of the film. The coated film was then dried in an oven at 52° C. An aqueous dilution of Serratia liquefaciens was prepared from an overnight culture to an approximate concentration of about 50 CFU/ml (Butterfield's buffer, Fisher Scientific). A sample of this solution (300 µl) was applied to the nutrient-coated film using the method of Example 3 to fill 420 microcompartments. The sample was incubated overnight at 37° C. Thirty-six fluorescent microcompartments were observed, corresponding to a calculated MPN of 39 (130/ml).

Example 8

Detection and Enumeration of Microorganisms (Detection Using pH Indicator and Nutrient Incorporated into Microcompartments)

This example demonstrates absorbance-based detection using an indicator that monitors the pH of the media.

VRB media containing the pH indicator phenol red (1 mg/ml, Sigma Chemical Company) was prepared as described in Example 3. This solution was incorporated into the microcompartments of a film as described in Example 7. An aqueous dilution (Butterfield's buffer, Fisher Scientific) of Serratia liquefaciens (approximately 50 CFU/ml) was applied to the film as described in Example 3 followed by overnight incubation at 37° C. Of the 420 microcompartments that were filled, 21 exhibited a yellow color, corresponding to an MPN value of 21 (70/ml).

Example 9

Enhanced Enzyme Kinetics Using Microcompartments (Enzyme+Fluorescent Indicator)

In this example, the same number of enzyme molecules (2.5 ng) were placed in a plurality of microcompartments ranging in size from 0.1 to 50 µl. Each well contained the same concentration of fluorescent indicator (0.25 mM). The production of fluorescence resulting from enzymatic hydrolysis of the indicator was measured simultaneously for each microcompartment using a CCD camera. An image was stored at each time point during the experiment. Quantitative fluorescence values for each microcompartment were obtained by loading the stored images into image processing software and averaging the intensity values over 4 pixels in the center of each microcompartment.

Detailed Procedure

A photolithographically etched magnesium tool was designed to provide inverted conical protuberances of increasing volume such that an embossed film prepared according to the procedure of Example 1A produced a film with microcompartments of 0.1, 0.5, 1.0, 3.0, 14, 20, and 50 µl.

A solution of alkaline phosphatase enzyme (0.1 mg/ml) was prepared in glycine buffer (50 mM, pH 10.4) and serially diluted into additional glycine buffer using the following sequential dilution scheme (in milliliters): 1:1; 1:4; 1:1; 1:2; 1:1.3; 1:1; 1:0.43; 1:15. An aliquot (100 µl) of each dilution was placed in adjacent microcompartments of a 96-microcompartment microtiter plate. A multi-channel pipettor was used to simultaneously add 100 µl of 4-methylumbelliferylphosphate indicator (0.5 mM in glycine buffer) to each microcompartment. An aliquot (0.1 µl) of the first dilution was placed immediately with a syringe into the microcompartment corresponding to this volume (0.1 µl). This was repeated for the subsequent six dilutions corresponding to volumes of 0.5, 1, 3, 14, 20, and 50 µl. Using this procedure, each microcompartment was filled with diluent containing 2.5 ng of enzyme in 0.25 mM of indicator. A background sample having microcompartments containing only indicator was also prepared.

After filing the microcompartments, the sample was placed in a covered petri dish and sealed with tape to prevent evaporation. The dish was placed inside an ultraviolet illumination and imaging device (UltraLum Corporation, 365 nm). CCD images were stored at the time intervals shown in FIG. 4. Fluorescence intensity values for each time point were obtained by averaging 4 pixels at the center of each microcompartment. Final values were obtained by averaging two duplicate experiments.

Figure 4:
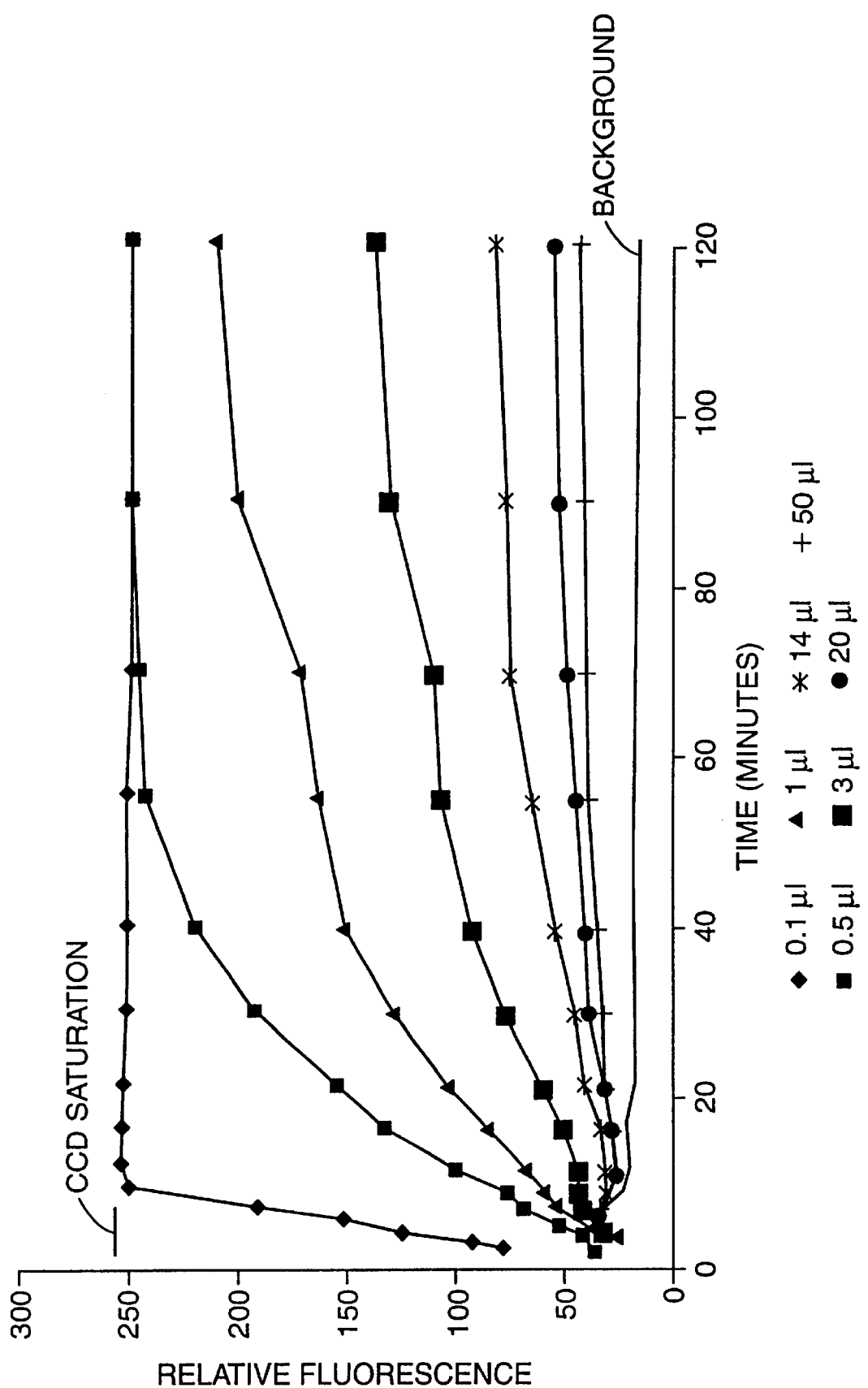
FIG. 4 is a graphic depiction of enhanced enzyme kinetics from use of microcompartments.

FIG. 4 shows (1) given the same number of enzyme molecules in each well, the kinetics of the reaction are significantly enhanced in the smaller microcompartments, and (2) the fluorescent signal for the detection system (CCD in this case) is enhanced in the smaller microcompartments. To illustrate this effect, 30 the background fluorescence of a microcompartment containing only indicator (no enzyme) is plotted on the graph. On a per-pixel basis, the signal is considerably higher (saturated for the smaller volumes) in the smaller microcompartments than in the larger microcompartments. Note that at the 2-hour time point the 50-µl intensity is 2.3×over background while the 1-µl value is 9.8×higher. Both the effects of enhanced reaction kinetics and enhanced fluorescent signal led to increasingly more rapid detection as the size of the microcompartments was decreased.

Example 10

Enhanced Microorganism Detection Using Microcompartments (Bacteria+Fluorescent Indicator)

In this example, the same number of bacteria (~5000 CFU) was placed in a plurality of microcompartments ranging in size from 1 to 50 µl. Each microcompartment contained the same concentration of fluorescent indicator (0.25 mM) in a nutrient growth media. The production of fluorescence resulting from enzymatic hydrolysis of the indicator was measured simultaneously for each microcompartment using a CCD camera.

Detailed Procedure

Polyethylene embossed films were prepared according to Example 9 with microcompartments designed to hold 1, 3, 7, 14, 20, and 50 µl of liquid. An overnight broth culture of E. coli ATCC 51813 (~$10^9$ CFU/ml in TSB) was serially diluted into VRB media containing 4-methylumbelliferyl-β-D-glucuronide (0.5 mg/ml) as described in Example 3. The dilutions were prepared such that ~5000 CFU were initially present in each well prior to incubation. The inoculated films were placed in petri dishes followed by incubation at 37° C. Relative fluorescence was measured at the time points shown in FIG. 5 using the CCD imaging system described in Example 9. Calculated times to reach a relative fluorescence value of 80 for each of the microcompartments are provided in Table 10a.

TABLE 10a

Detection of Bacteria (E. coli)

| Volume ($\mu$l) | Time (Hr) to Reach Relative Fluorescence of 80 |
|---|---|
| 1 | 6.2 |
| 3 | 7.1 |
| 7 | 7.5 |
| 14 | 8.7 |
| 20 | >9 |
| 50 | >9 |

Figure 5:
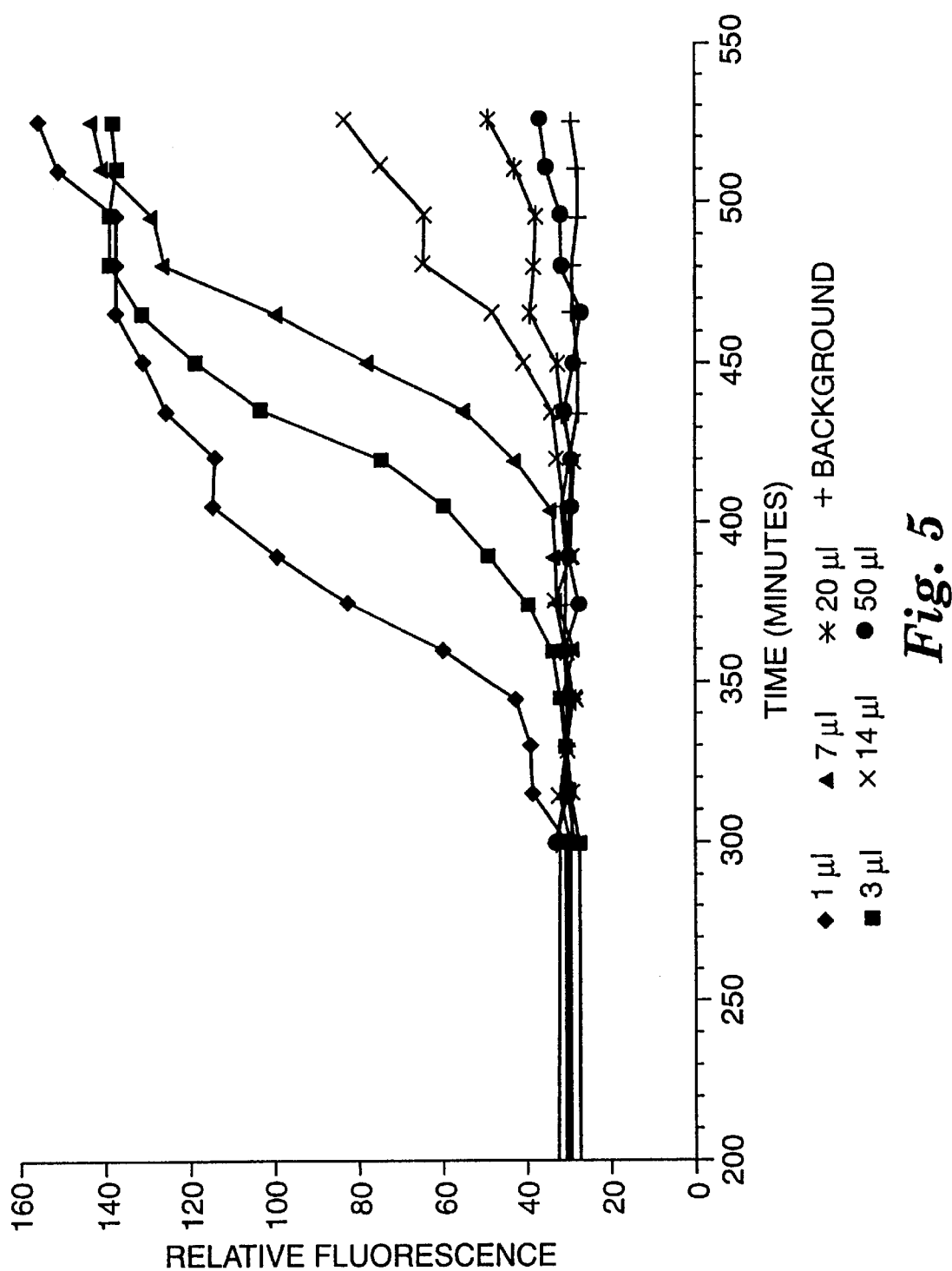
FIG. 5 is a graphic depiction of enhanced enzyme kinetics from use of microcompartments.

The results of this example as illustrated by the values in Table 10a and the graphical data of FIG. 5 show that fluorescence is observed significantly sooner in the smaller microcompartments than in the larger microcompartments.

Example 11

Detection and Enumeration of Microorganisms (Method Utilizing a Plurality of Microchannels)

The feasibility of utilizing film culture devices containing a plurality of covered microchannels to detect and enumerate bacteria was demonstrated in Section A (Single-Layer Film Culture Device) and Section B (Media-Coated Single Layer Film Culture Device) of this Example. The construction and inoculation of film culture devices containing multivolume "sets" of covered microchannels and containing multilayer film structures are described in Section C and Section D, respectively, of this Example.

A. Single-Layer Film Culture Device

Embossed film containing parallel V-groove microchannels was prepared as decribed in Example 1D and in U.S. Pat. No. 5,514,120. The resulting film was cover with a silicone PSA/PE top film (Example ID), thereby creating a series of parallel, covered microchannels having a triangular cross section with a base of approximately 6 mm and a height of approximately 0.75 mm. A flat "land area" of approximately 3 mm separated each microchannel, and provided an attachment surface for the cover film. The covered films were cut into 2-cm tall×5-cm wide strips with each strip (film culture device) containing 50 parallel, 2-cm long microchannels. Each channel had a volume of approximately 5 $\mu$l (total volume sampled approximately 250 $\mu$l). An overnight broth culture of E. coil ATCC 51813 was serially diluted into VRB media (Example 3), containing phenol red (0.5 mg/ml). The dilutions were prepared to the following approximate bacterial concentrations (CFU/ml): 10,000; 1,000; 100; and 10. One edge of the embossed film culture device was dipped into the sample and the fluid allowed to wick into the microchannels by way of capillary action. The top edge of the device was then sealed by dipping into melted paraffin to slow evaporation during inoculation. The bottom edge was left open. The samples were incubated overnight at 37° C. inside a humidified petri dish and then observed for red to yellow color changes. A yellow color along an individual channel indicated acid production from bacteria growth (glucose fermentation) within the channel. At the 10,000 CFU/ml and 1,000 CFU/ml dilutions, samples showed a yellow color in all 50 channels, suggesting that at least one organism partitioned into each channel during the wicking process. At the 100 CFU/ml dilution, 29 channels were yellow (bacteria present) and 21 channels were red (no bacteria), which corresponded to a calculated MPN of 179 (formula for MPN provided in Example 3). At the 10 CFU/ml dilution, only 3 channels were observed to be yellow, which corresponded to a MPN of 12. No color change was observed in the control samples which were prepared without the addition of E. coli.

B. Media-Coated Single-Layer Film Culture Device

A strip of embossed film (Example 11A) without the silicone PSA/PE top film was dipped into VRB media containing phenol red. The V-groove microchannels were allowed to fill, after which the film was removed from the nutrient media and dried at ambient temperature for about 30 minutes. The PSA/PE top film was applied to the embossed film to provide a media-coated film culture device, which was then dipped into an aqueous dilution of E. coli ATCC 51813 (~50 CFU/ml). The bacterial solution wicked into the media-coated microchannels via capillary action. After overnight incubation at 37° C., the embossed film culture device was observed to have 10 yellow channels and 40 red channels, corresponding to a MPN value of 44.

This example serves to demonstrate that bacterial nutrients can be incorporated into the microchannels of a film culture device, and that the device can then be used to directly sample an aqueous test solution.

C. Single-Layer Film Culture Device Containing Sets of Microchannels

A single-layer embossed film culture device containing multivolume sets of enclosed microchannels having volumes of 20 $\mu$l, 2 $\mu$l, and 0.2 $\mu$l was constructed as follows. The films for each set were embossed with tools of different configuration, covered with a top film as described in Example 11 A, and cut into strips of specific widths to give the desired microchannel volumes. The dimensions of the strips and volumes of the microchannels for each set are provided in Table 11a.

TABLE 11a

Single-Layer Film Culture Device Containing Sets of Microchannels

| Set | Strip Width (cm) | Microchannels (MC) Shape and Dimensions | | MC Volume ($\mu$l) | Total Volume (ml) (30 MC/Strip) (2 Strips/Set) | Counting Range (CFU/ml) |
|---|---|---|---|---|---|---|
| S1 | 2 | Rectangular: | 1.75-mm wide 0.65-mm tall | 20 | 1.2 | 0.8–205 |
| S2 | 1 | Rectangular: | 0.5-mm wide 0.4-mm tall | 2 | 0.12 | 7–1708 |
| S3 | 0.8 | Triangular: | 0.13-mm height 0.4-mm base | 0.2 | 0.012 | 70–17,083 |

The final single-layer film culture device was assembled by adhering two strips of each volume set (30 microchannels per strip) adjacent to each other at the base of a square petri dish ("Integrid" 100×15 mm, Becton Dickenson, Lincoln Park N.J.). The strips were attached using transfer tape (Scotch 300LSE Hi Strength Adhesive, 3M Co.) and placed approximately 2 mm apart.

The device was inoculated using a solution containing a food coloring dye to provide contrast. A transfer pipette was used to place the test solution in the "gutter area" between each set of strips. By tipping the device, fluid drained down the "gutter area" and filled the open-ended microchannels (positioned perpendicular to the "gutter area") by capillary action. Excess solution was contained by a strip of paper towel placed at the base of the device. By using the device of this example (60 microchannels per set) and the MPN formula outlined in Example 3, counting ranges for each of the three sets were calculated and are provided in Table 11a.

This example serves to demonstrate that a single-layer film culture device containing sets of microchannels can provide the basis for a bacterial enumeration test that is both highly sensitive and covers a very broad counting range.

D. Multilayer Film Culture Devices

Multilayer film structures were constructed in order to increase both the total volume of liquid sampled and the number of individual enclosed microchannels in the culture device. Two constructions were prepared by laminating together single-layer embossed films and are described in Table 11b. Single-layer films used in multilayer construction D1 contained parallel microchannels having a square cross section with sides approximately 0.2 mm×0.2 mm. Each microchannel was spaced approximately 0.1 mm apart. Single-layer films were cut into strips 1.5-cm wide×1-cm tall. A thin layer of adhesive (RD 1273, 3M Co.) was applied to the back of each strip, and the strips were stacked together to form a multilayer structure containing a plurality of microchannels. Construction D2 was assembled using the single-layer films described in Example 11A laminated together using a thin layer of adhesive (Super Strength Adhesive, 3M Co.)

TABLE 11b

Multilayer Film Culture Devices

| Device | Film Size | Construction | No of Channels (Vol./Channel) | Total Volume |
|---|---|---|---|---|
| D1 | 1.5 × 1 cm | 20 layers laminated together with RD 1273 Adhesive (3M Co.) | ~1000 (~0.05 µl) | 0.5 ml |

TABLE 11b-continued

Multilayer Film Culture Devices

| Device | Film Size | Construction | No of Channels (Vol./Channel) | Total Volume |
|---|---|---|---|---|
| D2 | 2 × 5 cm | 4 layers laminated together with Super Strength Adhesive (3M Co.) | ~200 (~5 µl) | 1 ml |

Detection of *E coli* ATC 51813 was demonstrated with the multilayer film device D2 (Table 11b) using serial dilutions of the bacteria in VRB media containing phenol red (Example 11A). One end of the device was dipped in the media, thereby filling each microchannel by capillary action. After overnight incubation at 37° C., color changes from red to yellow were observed in the microchannels containing growing bacteria by viewing the device in edge.

What is claimed is:

1. An assay device, comprising a substrate having a plurality of microchannels therein, wherein said microchannels have at least one assay reagent for enumerating microorganisms coated thereon and the volume of one microchannel is different than the volume of another microchannel.

2. The assay device of claim 1 wherein the substrate comprises a film having microchannels embossed thereon.

3. The assay device of claim 1 wherein the substrate comprises multiple layers of film having microchannels embossed thereon.

4. The assay device of claim 1 having multiple rows of microchannels.

5. The assay device of claim 1 having a plurality of sets of microchannels, each set having microchannels of uniform size and said sets varying in microchannel size.

6. The assay device of claim 1 wherein at least one microchannel has two ends and a middle and the cross section of the ends is smaller than the cross section of the middle.

7. The assay device of claim 1 wherein said at least one microchannel comprises an elongate hole.

8. The assay device of claim 1, wherein the plurality of microchannels comprise a plurality of capillary tubes.

* * * * *

UNITED STATES PATENT AND TRADEMARK OFFICE
CERTIFICATE OF CORRECTION

PATENT NO.    : 6,696,286 B1
DATED         : February 24, 2004
INVENTOR(S)   : Halverson, Kurt J.

It is certified that error appears in the above-identified patent and that said Letters Patent is hereby corrected as shown below:

Column 1,
Line 4, delete "08/905.481" and insert in place thereof -- 08/905,481 --;

Column 7,
Line 32, delete "," after the word "or";

Column 10,
Line 26, delete the word "to" after the word "plurality";

Column 13,
Line 40, delete "E coli" and insert in place thereof -- E. coli --;
Line 66, delete "In" and insert in place thereof -- 1n --;

Column 14,
Table 3a, Col. 1, Row 3, delete "$5 \times 10^{-4}$" and insert in place thereof -- $5 \times 10^{-6}$ --;
Table 3a, Col. 1, Row 4, delete "$1 \times 10^{-4}$" and insert in place thereof -- $1 \times 10^{-6}$ --;

Column 18,
Line 35, delete "30" after the word "effect,";

Column 19,
Line 38, delete "decribed" and insert in place thereof -- described --;
Line 39, delete "cover" and insert in place thereof -- covered --;
Line 42, delete "6" and insert in place thereof -- 0.6 --;
Line 44, delete "3" and insert in place thereof -- 0.3 --;
Line 51, delete "E.coil" and insert in place thereof -- E. coli --;

UNITED STATES PATENT AND TRADEMARK OFFICE
CERTIFICATE OF CORRECTION

PATENT NO. : 6,696,286 B1
DATED : February 24, 2004
INVENTOR(S) : Halverson, Kurt J.

It is certified that error appears in the above-identified patent and that said Letters Patent is hereby corrected as shown below:

Column 22,
Line 13, delete "E coli" and insert in place thereof -- E. coli -- ;
Line 21, delete "in" and insert in place thereof -- on --;
Line 40, after the word "wherein" insert -- the --;
Line 47, after the word "tubes" insert -- formed together --.

Signed and Sealed this

Eighth Day of March, 2005

JON W. DUDAS
*Director of the United States Patent and Trademark Office*